(12) United States Patent
Hoffman et al.

(10) Patent No.: US 7,858,659 B2
(45) Date of Patent: *Dec. 28, 2010

(54) REDOX THERAPY FOR TUMORS

(76) Inventors: Arnold Hoffman, Rehovot (IL); Lee M. Spetner, Jerusalem (IL); Michael Burke, Ramat Gan (IL)

(*) Notice: Subject to any disclaimer, the term of this patent is extended or adjusted under 35 U.S.C. 154(b) by 1138 days.

This patent is subject to a terminal disclaimer.

(21) Appl. No.: 10/621,326

(22) Filed: Jul. 18, 2003

(65) Prior Publication Data

US 2004/0018987 A1    Jan. 29, 2004

(51) Int. Cl.
A61K 31/27    (2006.01)
(52) U.S. Cl. .................... 514/483; 514/114
(58) Field of Classification Search ............ 514/34, 514/483, 114
See application file for complete search history.

(56) References Cited

U.S. PATENT DOCUMENTS 6,288,110 B1 * 9/2001 Marikovsky ............ 514/483
6,589,987 B2    7/2003 Kennedy

FOREIGN PATENT DOCUMENTS

WO    02056823 A2    7/2002

OTHER PUBLICATIONS

Huang et al. Mechanism and significance of increased glutathione level in human hepatocellular carcinoma and liver regeneration. The FASEB Journal, 2001, vol. 15, pp. 19-21; published online Nov. 9, 2000.*
Ali-Osman et al. Buthionine sulfoximine induction of gamma-L-glutamyl-L-cysteine synthetase gene expression, kinetics of glutathione depletion and resynthesis, and modulation of carmustine-induced DNA- DNA crosslinking and cytotoxcicity in human glioma cells. Mol. Pharm., 1996, vol. 49, pp. 1012-1020.*
Nagendra et al. Effect of disulfiram administration on rat brain glutathione metabolism. Alcohol, 1994, vol. 11, pp. 7-10.*
Gura et al. Systems for identifying new drugs are often faulty. Science, 1997, 278:1041-1042.*
Johnson et al. Relationships between drug activity in NCI preclinical in vitro and in vivo models and early clinical trials. British J. of Cancer, 2001, 84(10):1424-1431.*
Bailey et al. J. Natl. Cancer Inst., 1997, vol. 89, No. 23, pp. 1789-1796.*
Sharma et al. Clinical Cancer Research, Jul. 2001, vol. 7, pp. 1894-1900.*
Johnson et al. Neurosurgery, 1987, vol. 20, No. 4, pp. 577-583 (Abstract attached).*
R. Araya et al; "Hypoxia induces apoptosis in human neuroblastoma SK-N-MC cells by caspase activation accompanying cytochrome c release from mitochondria"; FEBS Lett (1990); vol. 439; pp. 168-72; Federation of European Biochemical Societies.
J. R. Babson et al; "Inactivation of glutathione reductase by 2-chloroethyl nitrosourea-derived isocyanates"; Biochem. Biophys. Res. Commun. (1978); vol. 83; pp. 745-762; Academic Press.

D. Cen et al; "Disulfiram induces apoptosis in human melanoma cells: a redox-related process"; Molec Cancer Ther (2002); vol. 1; pp. 197-204.
M.B. Cohen et al; "Characterization of the inhibition of glutathione reductase and the recovery of enzyme activity in exponentially growing murine leukemia (L1210) cells treated with 1,3-bis(2-chloroethyl)-1-nitrosourea." Biochem Pharm (1988); vol. 37; pp. 3317-3320; Pergamon Press PLC.
D.G. Cornwell et al; "Cytotoxicity of tocopherols and their quinones in drug-sensitive and multidrug-resistant leukemia cells"; Lipids (1998); vol. 33; pp. 295-301; AOCS Press.
J. Dai et al; "Malignant cells can be sensitized to undergo growth inhibition and apoptosis by arsenic trioxide through modulation of the glutathione redox system"; Blood (1999); vol. 93; pp. 268-77; The American Society of Hematology.
D. L. Duval et al; "Regulation of hepatic nitric oxide synthase by reactive oxygen intermediates and glutathione"; Arch Biochem Biophys (1995); vol. 316; pp. 699-706; Academic Press Inc.
H. Esterbauer et al; "Chemistry and biochemistry of 4-hydroxynonenal, malonaldehyde and related aldehydes"; Free Radic Biol Med (1991); vol. 11; pp. 81-128; Pergamon Press PLC.
T. M. Gottlieb et al; "p53 in growth control and neoplasia"; Biochim Biophys Acta (1996); vol. 1287; pp. 77-102; Elsevier Science B.V.
A. Hoffman et al; "Cessation of cell proliferation by adjustment of cell redox potential"; J Theoret Biol (2001); vol. 211; pp. 403-407; Academic Press.
D. E. Hutter et al; "Redox state changes in density-dependent regulation of proliferation"; Exp Cell Res (1997); vol. 232; pp. 435-438; Academic Press.
C. D. Kang et al; "Activation of c-jun N-terminal kinase/stress-activated protein kinase and the decreased ratio of Bcl-2 to Bax are associated with the auto-oxidized dopamine-induced apoptosis in PC12 cells"; Neurosci. Lett. (1998); vol. 256; pp. 37-40; Elsevier Science.
R. Kinscherf et al; "Induction of mitochondrial manganese superoxide dismutase in macrophages by oxidized LDL: its relevance in atherosclerosis of humans and heritable hyperlipidemic rabbits"; FASEB J (1997); vol. 11; pp. 1317-1328.
M. Kito et al; "Arsenic Trioxide-Induced Apoptosis and its Enhancement by Buthionine Sulfoximine in Hepatocellular Carcinoma Cel Lines"; Biochemical and Biophysical Research Communications (2002); vol. 291; pp. 861-867; Elsevier Science.
T. Lahusen et al; "Alsterpaullone, a novel cyclin-dependent kinase inhibitor, induces apoptosis by activation of caspase-9 due to perturbation in mitochondrial membrane potential"; Molec Carcinogen (2003); vol. 36; pp. 183-194.
Y. J. Lee et al; "Glucose deprivation-induced cytotoxicity and alterations in mitogen-activated protein kinase activation are mediated by oxidative stress in multidrug-resistant human breast carcinoma cells"; J Biol Chem (1998); vol. 273; pp. 5294-5299; The American Society for Biochemistry and Molecular Biology, Inc.

(Continued)

Primary Examiner—James D Anderson
(74) Attorney, Agent, or Firm—Ober, Kaler, Grimes & Shriver; Royal W. Craig

(57) ABSTRACT

The invention provides methods and compositions for treatment of tumors comprising administering to subject bearing a tumor an effective amount of at least one agent that decreases the $[GSH]^2/[GSSG]$ ratio in the malignant cells of said tumor, wherein said at least one agent is administered continuously to said patient for a period of time within the range of from about 15 to about 75 hours.

2 Claims, 2 Drawing Sheets

OTHER PUBLICATIONS

C. J. Li et al; "Potent inhibition of tumor survival in vivo by beta-lapachone plus taxol: combining drugs imposes different artificial checkpoints"; *Proc Natl Acad Sci USA*. (1999); vol. 96; pp. 13369-13374.

Y. Li et al; "Selective killing of cancer cells by beta-lapachone: direct checkpoint activation as a strategy against cancer"; *Proc Natl Acad Sci USA* (2003); vol. 100; pp. 2674-2678.

G. Lizard et al; "Glutathione is implied in the control of 7-ketocholesterol-induced apoptosis, which is associated with radical oxygen species production"; *FASEB J.* (1998); vol. 12; pp. 1651-1663.

S. Lord-Fontaine et al; "Enhancement of cytotoxicity of hydrogen peroxide by hyperthermia in chinese hamster ovary cells: role of antioxidant defenses"; *Arch Biochem Biophys* (1999); vol. 363; pp. 283-295; Academic Press.

A. Nicole et al; "Direct evidence for glutathione as mediator of apoptosis in neuronal cells"; *Biomed Pharmacother* (1998); vol. 52; pp. 349-355; Elsevier, Paris.

A. G. Paschka et al; "Induction of apoptosis in prostate cancer cell lines by the green tea component, (−)-epigallocatechin-3-gallate"; *Cancer Lett* (1998); vol. 130; pp. 1-7; Elsevier, Paris.

C. Ramachandran et al; "Differential sensitivity of human mammary epithelial and breast carcinoma cell lines to curcumin"; *Breast Cancer Res Treat* (1999); vol. 54; pp. 269-278; Kluwer Academic Publishers.

M. M. Rimpler et al; "Protection against hydrogen peroxide cytotoxicity in rat-1 fibroblasts provided by the oncoprotein Bcl-2: maintenance of calcium homoeostasis is secondary to the effect of Bcl-2 on cellular glutathione"; *Biochem J* (1999); vol. 340(Pt 1); pp. 291-297; Bochemical Society.

L. Rossi et al; "Quinone toxicity in hepatocytes without oxidative stress"; *Arch Biochem Biophys* (1986); vol. 251; pp. 25-35.

P. K. Rudra et al; "Acrolein cytotoxicity and glutathione depletion in n-3 fatty acid sensitive- and resistant human tumor cells"; *Anticancer Res* (1999); vol. 19; pp. 461-469.

C.K. Sen et al; "Fas mediated apoptosis of human Jurkat T-cells: intracellular events and potentiation by redox-active alpha-lipoic acid"; *Cell Death Differentiation* (1999); vol. 6; pp. 481-491; Stockton Press.

R. Smaaland et al; "Glutathione content in human bone marrow and circadian stage relation to DNA synthesis"; *J Natl Cancer Inst* (1991); vol. 83; pp. 1092-1098.

A. C. Smith et al: "Pharmacokinetics of Buthionine Sulfoximine (NSC 326231) and Its Effect on Melphalan-induced Toxicity in Mice"; *Cancer Research* (1989); vol. 49; pp. 5385-5391.

S. Tamrakar et al; "Role of pRB dephosphorylation in cell cycle regulation" *Frontiers in Bioscience* (2000); vol. 5; pp. D121-D137.

D. E. Thornton et al; "Antioxidant and cytotoxic tocopheryl quinones in normal and cancer cells"; *Free Radic Biol Med* (1995); vol. 18; pp. 963-976; Pergamon Press.

U. Wullner et al; "Glutathione depletion and neuronal cell death: the role of reactive oxygen intermediates and mitochondrial function"; *Brain Research* (1999); vol. 826; pp. 53-62; Elsevier Science B.V.

A. Yamauchi et al; "Control of cell cycle progression in human natural killer cells through redox regulation of expression and phosphorylation of retinoblastoma gene product protein"; *Blood* (1997); vol. 89; pp. 4092-4099.

A. Zetterberg et al; "Kinetic analysis of regulatory events in G1 leading to proliferation or quiescence of Swiss 3T3 cells"; *Proc Natl Acad Sci USA* (1985); vol. 82; pp. 5365-5369.

A. Zetterberg et al; "Cell cycle progression and cell growth in mammalian cells"; *Frontiers in Molecular Biology: Cell Cycle Control* (1995); pp. 2066-2085; Oxford University Press, Oxford, UK.

A. Zetterberg et al; "What is the restriction point?"; *Curr Opinion in Cell Biology* (1995); vol. 7; pp. 835-842; Current Biology Ltd.

J. R. Zhou et al; "Soybean phytochemicals inhibit the growth of transplantable human prostate carcinoma and tumor angiogenesis in mice"; *J Nutrition* (1999); vol. 129; pp. 1628-1635; American Society for Nutritional Sciences.

F. Q. Schafer et al;"Redox environment of the cell as viewed through the redox state of the glutathione disulfide/glutathione couple"; *Free Rad Biol Med* (2001); vol. 30; pp. 1191-1212.

Bailey, et al., "Phase I clinical trail of intravenous L-buthionine sulfoximine and melphalan: an attempt at modulation of glutathione", *Journal of Clinical Oncology*, Jan. 1994, vol. 12, No. 1, 194-205.

Noda, et al., "Induction of Mild Intracellular Redox Imbalance Inhibits Proliferation of CaCo-2 Cells", *FASEB Journal*. Oct. 2001, vol. 15, 2131-2139.

* cited by examiner

REDOX THERAPY FOR TUMORS

FIELD OF THE INVENTION

The present invention is of a treatment for defective cells, such as tumor and malignant cells, by altering the redox state or environment of the cell, preferably continuously maintaining this altered state for an appropriate time duration, and in particular, of such a treatment in which the balance of GSH (glutathione) to GSSG (glutathione disulfide) is altered.

ABBREVIATIONS: BCNU: N,N'-bis(2-chloroethyl)-N-nitrosourea; BSO: buthionine sulfoximine; Carmustine: BCNU; CCP: cessation of cell proliferation; E: intracellular redox potential; EA: ethacrynic acid; GCL: γ-glutamylcysteine synthetase; GCS: GCL; GR: glutathione reductase; GS: glutathione synthetase; GSH: glutathione; GSSG: glutathione disulfide; RB: retinoblastoma protein; ROS: reactive oxygen species.

BACKGROUND OF THE INVENTION

The redox state of a cell refers to the balance between oxidative processes and reducing processes. The energy released by oxidative processes is used by the cell to build cellular and tissue structures, and to operate and maintain such structures. The term redox state has typically been used to refer to two molecules between which electrons may be traded, and which are referred to as a "redox couple". An example of such a couple is made up of the two molecules glutathione (GSH) and its oxidized form, glutathione disulfide (GSSG), which help to determine the balance between oxidative and reducing processes, and hence the redox state or environment of the cell. Another redox couple comprises NADPH and $NADP^+$. The balance between the oxidized and reduced forms of these couples may have many important biological effects, particularly with regard to the growth and proliferation of the cell.

Without wishing to rule out other mechanisms, it can be assumed that the redox state of the cell has some measure of control over the proliferative behavior of the cell, and in particular to the induction of cessation of cell proliferation (CCP), as explained in greater detail below.

One way to describe the redox state or environment of the cell is through the Nernst Equation. Changes in the intracellular redox potential, E, are, according to the Nernst equation, proportional to changes in $\log\{[GSH]^2/[GSSG]\}$, where [GSH] and [GSSG] are the concentrations of GSH and GSSG, respectively. As [GSH] decreases, E increases (Hutter et al., 1997).

Decreasing the level of GSH increases the redox potential of the cell, and has been observed to lower the rate of cell proliferation. Normal actively proliferating (foreskin) fibroblasts have been observed to have an average E of about −222 mV, which is about 10 mV lower than that observed for neoplastic fibrosarcoma cells, where the average E has been observed to be about −211 mV (Hutter et al., 1997). Proliferative behavior appears to be associated with the redox potential of the cell. Decreasing the level of GSH increases the redox potential of a cell, and has been shown to result in a decrease, or cessation of, cell proliferation. Again, without limiting the process to a single mechanism, we suggest that such behavior is at least partially mediated through effects on the retinoblastoma (RB) protein, considered to be a master regulator of cell cycle, differentiation and apoptosis.

The human RB protein is a nuclear phosphoprotein spanning 928 amino acids in length that is expressed in every tissue type examined. This protein appears to be the major player in a regulatory circuit in the late $G_1$ (growth) phase, the so-called restriction point R, that defines a timepoint in $G_1$ at which cells are committed to enter S (DNA replication) phase and no longer respond to growth conditions. Moreover, RB is involved in regulating an elusive switch point between cell cycle, differentiation and apoptosis.

Functional interactions exist between RB and the three D cyclins, together with their associated kinases. Cyclins function to activate cyclin-dependent kinases, which facilitate adding phosphates onto other molecules that play a role in cell-cycle progression. The phosphorylation of RB, via cyclin-dependent kinases, correlates with an inactivation of its ability to arrest cellular division. Specifically, if RB is inactivated, a cell will proceed through the cell cycle, multiplying unchecked until the RB is again activated. Herein lie the implications for cancer biology.

When the GSH concentration in NK3.3 cells is sufficiently decreased, and hence E is sufficiently increased, the RB protein in these cells cannot be phosphorylated and the cells cease to proliferate. Dephosphorylated RB traps the transcription factors that are necessary for the generation of the cyclins required for cell proliferation, resulting in a cyclin-poor cell. When GSH is restored, E is decreased, RB can be phosphorylated and these cells proliferate (Yamauchi et al., 1997). This critical value of E which induces cessation of cell proliferation (CCP), is designated $E_{CCP}$. Arrest in $G_{1pm}$, the first part of the $G_1$ phase of the cell cycle (the postmitotic interval of $G_1$ that lasts from mitosis to the restriction point R), prevents the cell from proceeding to the second part of the $G_1$ phase, $G_{1ps}$, (the pre-S phase interval of $G_1$ that lasts from R to S), as well as to S and to subsequent phases of the cell cycle. When this arrest has persisted for a few hours, then the duration required for apoptosis induction is achieved. Consequently, as the cancer cells that are in $G_{1pm}$, are unable to enter $G_0$ (Zetterberg et al., 1995), they will undergo apoptosis. In contrast, normal cells in $G_{1pm}$ can, and do, enter $G_0$ and are able to stay there indefinitely. A model of the normal and cancer cell cycles is summarized in Scheme FIG. 1, which shows the cycle of a normal proliferating cell (black) and of a tumor cell (gray). Notice that the cell-cycle period for the tumor cell is shorter than that of the normal cell by the duration of G1 pm, which the tumor cell skips. The redox potential E is shown for each type of cell. The redox potential of the normal cell cycles between a high value during G1 pm and a low value during $G_2$ and half of M. The transitions between these two levels are shown as dashed lines because of our lack of knowledge of the precise time profiles of these transitions. The redox potential of the tumor cell is constant throughout the cell cycle and is below the threshold Eccp. The redox potential of the normal proliferating cell cycles lies above and below the threshold.

Hutter et al. (1997) have studied the redox-state changes in density-dependent regulation of normal and malignant cell proliferation in the presence of modulators of GSH synthesis and have suggested a possible interrelationship between the redox potential and cell proliferation. Lee et al. (1998) showed that glucose deprivation-induced cytotoxicity is mediated by oxidative stress with formation of intracellular hydrogen peroxide in human breast carcinoma cells. Rossi et al. (1986) showed that the cytotoxicity of dimethyl- and tri-methyl-benzoquinones to normal hepatocyte cells was due to a decrease in the [GSH] due to the formation of a quinone conjugate without oxidation to GSSG, while the addition of duroquinone, a tetramethylbenzoquinone, stimulated GSH oxidation and was only cytotoxic when catalase or glutathione reductase (GR) was inactivated. Smaaland et al., 1991, found a statistically significant correlation between the GSH content and the fraction of bone marrow cells in DNA synthesis.

There are many approaches for treating tumors. Some of these approaches are, to some extent, selective, such as the surgical removal of the tumor. In general, surgery is effective if the tumor has not spread and all the malignant cells have been removed. Other approaches are less selective and include radiation and chemotherapy, which usually affect normal cells as well. An agent is considered to provide a selective result if it mostly affects the cancer cells of the tumor, but does little, if any, harm to the adjacent normal cells of the tissue.

Many of the classical chemotherapeutic agents are usually more effective when the cancer cells in the tumor are rapidly proliferating. Some of the known cytotoxic agents such as vincristine, vinblastine, etoposide, methotrexate, 5-fluorouracyl, cytarabine, cisplatine, generally affect DNA during cell proliferation, primarily killing cancer cells rather than the relatively slowly proliferating normal cells. But this selectivity factor is not operative when treating slowly proliferating cancer cells. Other anti-cancer agents have been developed such tamoxifen, taxol, flavopiridol, angistatin, retinoic acid (all-trans and 9-cis), which do not affect the DNA during cell proliferation. Various mechanisms have been suggested for those two classes of agents, hereby designated as standard chemotherapeutic agents. There is, however, uncertainty in the conventional wisdom of the background art about the precise mechanisms involved. In general, anti-cancer agents, at their effective concentrations, are considered activators or triggers that trigger the formation of a sequence of various entities such as p21, which induce apoptosis (Li 1999; 2003). The concentrations of standard chemotherapeutic agents currently used for cancer treatment are limited usually to less than 5 µM (Ramachandran et al., 1999) in order to minimize injury to normal cells.

Reactive oxygen species (ROS), as generated by radiation, for example, are believed to cause mutations that produce cancer. There appears to be a consensus that antioxidants such as GSH, which can scavenge or otherwise neutralize the ROS, are required to prevent and treat cancer (Dai et al., 1999, Sen et al., 1999). If an antioxidant is defined as an agent that decreases E, by increasing the $GSH^2/GSSG$ ratio and, vice-versa, an oxidant as an agent that increases E, by decreasing the $[GSH]^2/[GSSG]$ ratio, some of the agents currently used as anticancer drugs or described in the literature as mentioned below, are clearly not acting as antioxidants.

In-vitro studies of treatment of tumor cell lines with several compounds have been carried out and have shown promising results, yet the basic mechanism of how these various compounds work remains obscure. In recent reports described hereinbelow, most experiments were performed with cell lines, that intrinsically involve relatively rapid cell proliferation, and the results with these various agents may not demonstrate their selectivity or their effectiveness in more slowly growing tumors.

Dai et al. (1999) introduced $As_2O_3$ into various cell lines. The resulting intracellular GSH content had a decisive effect on $As_2O_3$-induced apoptosis, the tendency to apoptosis increasing as the GSH content of the cell decreased. GSH forms an adduct with arsenic (As), viz., $As(GS)_3$. These researchers experimentally varied the GSH content of the various cells with BSO (buthionine sulfoximine), which inhibits gamma-glutamylcysteine synthetase, GCS, a key enzyme in GSH biosynthesis. Tendency to apoptosis increased as GSH content decreased. By itself, BSO, which caused a decrease in [GSH] of 70% in the cell, did not induce significant apoptosis, but rendered the malignant cells more sensitive to $As_2O_3$. The authors did not report any measured value of [GSSG]. Normal cells showed the least apoptosis.

Nicole et al. (1998) showed that the introduction of BSO to neuroblastoma cells, decreasing their GSH content by 98%, and induced apoptosis. Here, too, they did not report any measured value of [GSSG]. They concluded that, with these cells, there was a cause-and-effect relationship between decreasing GSH and apoptosis induction.

Sen et al. (1999) introduced α-lipoic acid into both Jurkat T-cell leukemia cells and normal lymphocytes, and noticed that the leukemia cells underwent apoptosis, whereas the normal cells did not. They suggested that the induction of apoptosis by α-lipoic acid was because this acid is a sulfur-containing antioxidant that provides strong reducing power and leads to the reduction of protein thiols.

Lizard et al. (1998) reported that the introduction of 7-ketocholesterol to U937 cancer cells induced apoptosis. They found that apoptosis was enhanced by the addition of BSO and inhibited by the addition of NAC (N-acetyl-L-cysteine), a cysteine precursor which penetrates the cell and is converted by deacetylation to cysteine, which is a GSH precursor. The authors suggested that oxidative processes are involved in 7-ketocholesterol-induced cell death.

Rudra et al. (1999) reported that the introduction of acrolein induced cytotoxicity in various cancer cell lines, such as A-427 and A-172. They demonstrated that the sensitivity to growth inhibition increases as GSH decreases. They also reported that A-427 is highly sensitive to docosahexaenoic acid, and that acrolein potentiates the cytotoxic effect of this acid. These researchers reported that acrolein depletes thiols and is highly toxic to both normal human bronchial fibroblasts and human bronchial epithelial cells in the respiratory system.

Rossi et al, (1986), Thornton et al. (1995) and Cornwell et al (1998), introduced various quinones or quinone precursors to both normal cells, such as smooth muscle cells and hepatocytes, and to leukemic cells. Rossi et al. (1986) concluded that, when GSH decreased by 90-95% of the original amount in the hepatocytes, significant cytotoxicity was induced. They all concluded that the quinones formed a Michael Adduct with the GSH.

Ramachandran et al. (1999) introduced curcumin to both human mammary epithelial cells (MCF-10A) and breast carcinoma (MCF-7/TH) cell lines, and concluded that the induction of apoptosis is due to the effect of the curcumin on some of the genes associated with cell proliferation.

Zhou et al. (1998) introduced soy isoflavones to human prostate carcinoma cells and normal vascular endothelial cells. They suggested that these soy products inhibit experimental prostate tumor growth through a combination of direct effects on tumor cells and indirect effects on tumor neovasculature.

Paschka et al. (1998) induced apoptosis of prostate cancer cell lines by introducing green tea phenols including (−)-epigallocatechin-3-gallate.

With respect to tumors in general, especially slowly growing tumors, there is a dire need for agents that can selectively cause the cessation of cell proliferation (CCP), either as a result of cell arrest or apoptosis, similar to the effect of radiation on cells. Radiation is a p53 inducer, and the latter, in turn, induces p21, which can then combine with or otherwise inactivate the cyclins normally required for cell proliferation. As a result, the cyclin-poor cell undergoes cell cycle arrest or apoptosis (Gottlieb & Oren, 1996). In many cases, however, radiation is not completely selective, since it affects adjacent normal tissues; in addition, it causes unpleasant and serious side effects. Thus, more selective and effective treatments for cancer are required.

Throughout this specification, various scientific publications and patents or published patent applications are referenced. Full citations for these references may be found at the end of the specification immediately preceding the claims. The disclosure of all these publications in their entireties is hereby incorporated by reference into this specification in order to more fully describe the state of the art to which this invention pertains. Citation or identification of any reference in this section or any other part of this application shall not be construed as an admission that such reference is available as prior art to the invention.

SUMMARY OF THE INVENTION

It has now been discovered by the present inventors that cessation of cell proliferation (CCP) and apoptosis of malignant cells can be selectively achieved by increasing the intracellular redox potential, E, above $E_{CCP}$, and maintaining this higher E for an appropriate duration of time such as to induce selective apoptosis of the cancer cells.

The present invention relates, in one aspect, to a method for treatment of a tumor-bearing subject which comprises administering to said subject a pharmaceutically effective amount of at least one agent that controls the redox state or environment of the malignant cells of said tumor such as to cause cessation of cell proliferation or apoptosis of the malignant cells.

In one preferred embodiment, the method of the present invention comprises administering to said subject an effective amount of at least one agent that decreases the $[GSH]^2/[GSSG]$ ratio in the malignant cells of said tumor, the at least one agent imposing on the cancer cells an E above $E_{CCP}$, and maintaining this increased E for an appropriate duration of time that corresponds to at least the time of the cell cycle period, thus requiring a continuous administration of said at least one agent for a period of time within the range of from about 15 to about 75 hours.

In another preferred embodiment, the invention provides methods and compositions for the treatment of cancer comprising a synergistic combination of two or more different agents that affect E through affecting [GSH] and [GSSG] via different mechanisms and kinetics, as will be defined in the Detailed Description of the Invention section hereinbelow.

DETAILED DESCRIPTION OF THE INVENTION

The background art does not teach or suggest a treatment for malignancies on the basis of altering redox potential in the cell. The background art does not teach or suggest agents, or the effective concentrations thereof, nor the required continuous effective contact of said agents during an appropriate time with tumor tissue, that will induce selective cessation of cell proliferation or cell apoptosis.

The present invention overcomes these deficiencies of the background art by providing a treatment for malignancies and/or otherwise controlling the growth and/or proliferative behavior and/or other abnormal biological functions of a cell or tissue displaying malignant properties, through the control of the redox state of the cell or the cellular redox environment.

In the most preferred embodiment of the present invention, control of the redox state of the malignant cells refers to the control of the cellular contents of GSH and GSSG, or more particularly of the $[GSH]^2/[GSSG]$ ratio, whereby this is achieved by employing at least one agent that decreases the $[GSH]^2/[GSSG]$ ratio in the cancer cells in the tumor and raises the intracellular redox potential E above $E_{CCP}$, the redox potential where cessation of cell proliferation occurs.

According to the present invention, the intracellular redox potential E is expressed in millivolts (mV) and is calculated in terms of the concentrations of the members of the dominant redox couple pair GSH and GSSG according to the Nernst equation, as follows:

$$E = E_0 - 30 \log [GSH]^2/[GSSG]$$

wherein $E_0$ is the standard potential of glutathione.

The present invention thus specifically teaches away from the background art, as the present invention teaches that effective oxidants, i.e. those agents that raise the E of the cancer cells in the tissue, should be used for tumor treatment in concentrations that raise E above $E_{CCP}$, and that damage to the DNA is not the primary cause of cell death in these cases as with many classical chemotherapeutic agents, but rather cell death is the result of the cell undergoing apoptosis in which the DNA is damaged through the cell's own programmed death.

Figure 1:
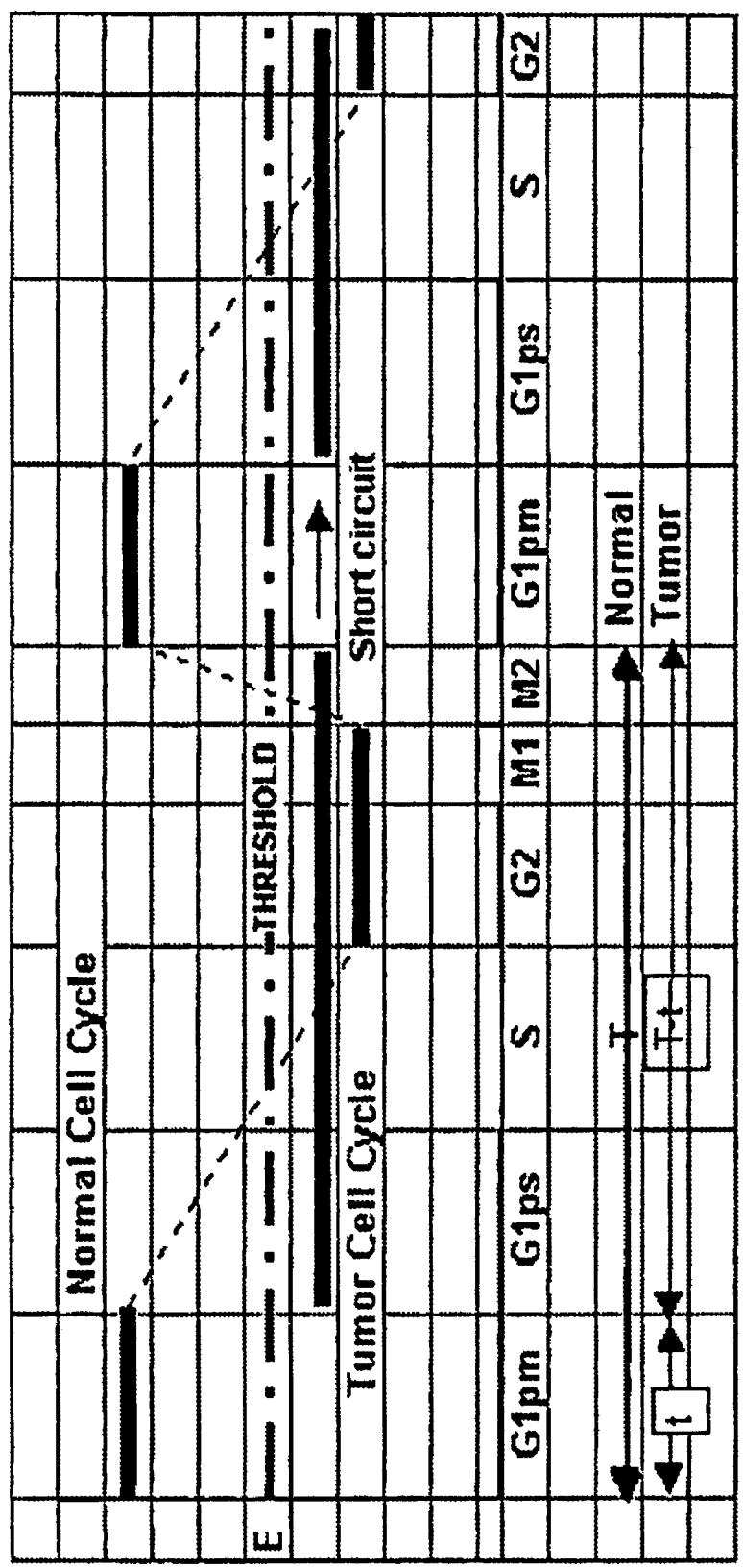
FIG. 1 is a model of the normal and cancer cell cycles.

Furthermore, in a most preferred embodiment, the agents that can be used according to the invention must be in continuous contact with the cancer tissue for an appropriate time such that their effect of maintaining E above Eccp is maintained continuously throughout the effective contact time for the duration required to ensure that the cancer cells in the all phases of the cell cycle have had time to reach the $G_{1pm}$ phase (the postmitotic interval of $G_1$ that lasts from the restriction point R to S), and remained in $G_{1pm}$ for a time, t, corresponding to the duration of $G_1$, i.e., a few hours (according to Zetterberg et al., 1995, $G_{1pm}$ is remarkably constant in length and its duration is about 23% of mean of the normal cell cycle time). This parameter, herein designated tau, of the administration protocol of the agent of the invention, corresponds to at least one, preferably about 2-3, the normal cell-cycle time, T (See FIG. 1), i-e., from about 15 to about 72 hours. This multiple pass through the cell cycle period is required to allow the cells that were not trapped in $G_{1pm}$ after T, to become trapped after 2 T or 3 T. Thus, in cancer cells, CCP is manifested as either cell-cycle arrest or apoptosis, depending upon the time of contact between the agent and the cancer cells.

Thus, according to the present invention, the at least one agent that decreases the $[GSH]^2/[GSSG]$ ratio in the malignant cells should be administered such that E remains above $E_{CCP}$ for from about 15 to about 72 hours, in order to achieve the optimum results. The time will depend on the tissue, since the cell cycle time is different from tissue to tissue, from the type of tumor and the severity of the disease. There is, however, an upper time limit for the duration of the treatment, because of the vulnerability of an organism to an E that prevents normal cells from exiting $G_{1pm}$ when required; e.g. healing of wounds.

In the prior art references mentioned in the Background section hereinabove, the authors of those references have attributed to a variety of causes the results of the experiments in terms of antiproliferative effect or apoptosis. However, until the present invention, it has not been recognized that there is a common cause underlying most of the experiments that resulted in CCP, namely that there exists a threshold intracellular redox state or redox potential, $E_{CCP}$, and that agents that decrease GSH concentration can increase E above $E_{CCP}$, inhibit RB phosphorylation, and induce CCP, which can lead to apoptosis.

Moreover, the teaching of the present invention is contrary to the background art. The background art teaches that antioxidants should be used both to prevent and to treat tumors (e.g. Sen et al., 1999), whereas the present invention teaches that agents that are effectively prooxidants are required to treat tumors, where a prooxidant is defined as an agent that increases the intracellular redox state or redox potential to a more oxidizing value, i.e., a higher value of E.

The concept of the present invention as defined above has not been described or even suggested in the prior art. However, it can find support when data published in the prior art are analyzed with respect to the relationship of the reported E values to the threshold $E_{CCP}$. For example, Table 1 in Hutter et al., 1997, describes the effect of modulators of GSH synthesis on proliferation of normal fibroblast cells. In these studies, culture density was tabulated as a function of redox potential. It can be deduced from the data in Table 1 that the average value of E (redox potential) that corresponds to the threshold for cessation of cell proliferation ($E_{CCP}$) of fibroblasts is −205±15 mV. Below $E_{CCP}$, the cells proliferate; above $E_{CCP}$, cells do not proliferate and the cell density decreases more than 50%.

Lee et al., 1998, studied glucose deprivation-induced cytotoxicity in multidrug-resistant human breast carcinoma cells and measured the changes in [GSH] and [GSSG] as a result of oxidative stress induced by glucose deprivation. They reported that, although there was a large spread in the data, there was a definite difference between the test and control. The changes in the mean values of [GSH] and [GSSG] in these cancer cells, produced by glucose deprivation, correspond to a change in E of 3 mV. As the average E of cancer cells is about −211 mV (as deduced from data of Hutter et al. 1997), then, if the change in the mean value of E is applied, $E_{CCP}$=+3−211, or about −208 mV. Thus, in correspondence with the analysis of the results of Hutter et al. (1997), an artificial increase of E to $E_{CCP}$, is seen here to induce CCP.

Thus, according to the present invention, selective induction of apoptosis of cancer cells in a tumor tissue can be obtained by imposing on this tissue, and maintaining effectively continuously, for a time, defined as tau, a well-poised redox buffer set several mV above $E_{CCP}$, e.g. at about −190 to −200 mV. This can be achieved with at least one agent that decreases the $[GSH]^2/[GSSG]$ ratio, for example and more preferably, by administering one or more GSH-decreasing agents for a time such as to achieve apoptosis. It should be noted that the required effective contact time can be much longer that the actual contact time of the agent with the cell.

According to one aspect, the present invention provides a method of treating a tumor in a subject, which comprises administering to said subject a pharmaceutically effective amount of at least one agent that decreases the $[GSH]^2/[GSSG]$ ratio in the malignant cells of said tumor, wherein said at least one agent is administered continuously to said patient for a period of time within the range of from about 15 to about 75 hours.

A "pharmaceutically effective amount" as defined herein is the amount administered to maintain continuously the E of the cancer cell at about −190 to −200 mV for a time, tau, which retards the proliferation of a tumor and/or causes regression of a tumor, and constrains potential or actual harm to normal tissues in the organism. When a combination of agents is used, the combined amount that is pharmaceutically effective is a quantity of the two or more agents which, when combined and administered to maintain continuously the E of the cancer cell at about −190 to −200 mV for a time, tau, retards the proliferation of a tumor and/or causes regression of a tumor by inducing cessation of cell proliferation, CCP, which ultimately leads to apoptosis, while constraining potential or actual harm to the normal tissues in the organism.

The approach of the present invention has two types of built-in selectivity. First, since normal proliferating cells may have lower E values (higher [GSH]) than cancer cells, as has been observed in fibroblasts and fibrosarcoma cells (Hutter et al., 1997), the addition of appropriate amounts of GSH-decreasing agents to a tumor-containing tissue can increase the E of the cancer cells to or beyond $E_{CCP}$, whereas the E of normal proliferating cells in the tissue can still remain below $E_{CCP}$ (Hoffman et al., 2001). Second, if normal cells are trapped in $G_{1pm}$, they can enter $G_0$ where they may remain indefinitely. Consequently, the introduction of agents according to the invention will not harm normal cells. Cancer cells, on the other hand, cannot enter $G_0$. Instead, after several hours in $G_{1pm}$, they undergo apoptosis.

In one preferred embodiment of this aspect, said agent is a GSH-decreasing agent, or a precursor thereof, such as, but not limited to, β-alanylcysteamine, arsenic trioxide, ascorbic acid, buthionine sulfoximine, camptothecin, capsaicin, carmustine, daunorubicin, diamide, diethyl maleate, disulfiram, dopamine, doxorubicin, duroquinone, epothilone A, epothilone B, erbstatin, ethacrynic acid, etoposide, gemcitabine, hydrogen peroxide, an isoflavone such as, but not limited to, catechin, daidzein, dicumarol, (−)epicatechin, flavopiridol, genistein, β-lapachone, myricetin and rotenone, α-lipoic acid, mifepristone, oxidized low density lipoproteins (ox-LDLs), a polyunsaturated fatty acid (PUFA), propargylglycine, an unsubstituted or partially substituted quinone such as, but not limited to, anthraquinone, benzoquinone, 2-methyl-, 2,6-dimethyl, 2,5-dimethyl, and 2,3,5-trimethyl-benzoquinone, and γ- and δ-tocopherolquinones; N-(4-hydroxyphenyl) retinamide, retinoic acid, rotenone, staurosporine, a ubiquinone (2,3-dimethoxy-4-substituted-5-methyl-benzoquinones) such as ubiquinone 50 (Coenzyme $Q_{10}$), an α,β-unsaturated aldehyde such as, but not limited to, cinnamaldehyde, a 4-hydroxy-$C_5$-$C_9$-alkenal (e.g. 4-hydroxypentenal, 4-hydroxy-hexenal, 4-hydroxy-heptenal, 4-hydroxy-nonenal), and a phenol, such as, but not limited to, curcumin, (−) epigallocatechin-3-gallate, resveratrol (3,5,4'-trihydroxy-trans-stilbene), γ-tocopherol, δ-tocopherol, yakuchinone A, and yakuchinone B.

In one embodiment, the GSH-decreasing agent may be administered together with at least one standard chemotherapeutic drug such as, but not limited to, vincristine, vinblastine, melphalan, methotrexate, 5-fluorouracyl, cytarabine, cisplatine, tamoxifen, taxol, angistatin, and/or in conjunction with a non-drug treatment for cancer such as radiotherapy.

The term "tumor" as used herein encompasses all types of cancers and malignant tumors including non-solid tumors such as leukemias and lymphomas, but, preferably, it refers to solid tumors including, but not being limited to, bladder, bone, brain, breast, cervical, colon, esophageal, kidney, laryngeal, liver, lung, melanoma, ovary, pancreas, prostate, rectal, skin, testicular, and uterine tumors. Moreover, the term "tumor" encompasses primary tumors, secondary tumors, and metastases thereof in the same organ or in another organ. It is envisaged that this invention will work preferably in tumor cells in which the RB protein is operative. If, however, elevated E stops proliferation more by inactivating the transcription factors than by preventing phosphorylation of pRB, then the invention will work even if pRB is not operative.

The terms "treatment of a tumor" and "anti-tumor" as used herein refer to a treatment or a composition that retards the proliferation of a tumor and/or causes regression of a tumor.

According to the present invention, the GSH-decreasing effect may be obtained by employing agents that perform at least one of the following activities: (i) oxidize GSH to GSSG; (ii) form an adduct or conjugate with GSH; (iii) inhibit the γ-glutamylcysteine synthetase (GCS or GCL) enzyme, that catalyzes the rate-limiting step in GSH synthesis; (iv) inhibit glutathione reductase (GR), the enzyme that catalyzes the reduction of GSSG back to GSH via oxidation of NADPH; or (v) diminish the precursor of GSH, or (vi) the agent may be a precursor of any one of the agents (i) to (v).

In one embodiment of the invention, the agent is a GSH-oxidizing agent, of the class (i) above, or precursors thereof, including, but not being limited to, disulfiram; hydrogen peroxide precursors (that generate hydrogen peroxide in vivo) such as ascorbic acid or dopamine, that autooxidize producing high levels of hydrogen peroxide, or a non-drug treatment such as glucose deprivation, radiation therapy or hyperthermia; α-lipoic acid; oxidized low density lipoproteins (ox-LDLs), and certain fully substituted quinones such as duroquinone (2,3,5,6-tetramethyl-benzoquinone), ubiquinones (2,3-dimethoxy-4-substituted-5-methyl-benzoquinones) such as ubiquinone 50 (coenzyme $Q_{10}$), and β-lapachone.

In another embodiment, the agent forms an adduct or conjugate with GSH, of the class (ii) above, or precursors thereof, including, but not being limited to, a Michael acceptor (a molecule that has a —C=C— group adjacent to an electron withdrawing group, preferably a carbonyl group, but that can be also a cyano or a nitro group), which is an electrophile and forms a Michael adduct with GSH, a Michael donor, which is a nucleophile, but other types of conjugation are also envisaged by the invention. Examples of Michael acceptors and other conjugating agents include, without being limited to, the following agents: diethylmaleate (Duval et al., 1995); ethacrynic acid (EA) (Schafer & Buettner, 2001), that conjugates GSH via glutathione-S-transferase and prevents the use of GSH, but not its synthesis; epothilones A and B; α,β-unsaturated aldehydes such as cinnamaldehyde, 4-hydroxyl-$C_5$-$C_9$-alkenal (e.g. 4-hydroxyl-pentenal, 4-hydroxyl-hexenal, 4-hydroxyl-heptenal, 4-hydroxyl-nonenal) and their precursors polyunsaturated fatty acids (PUFA) (Rudra et al., 1999; Esterbauer et al., 1991); unsubstituted or partially substituted quinones such as, but not limited to, anthraquinone, benzoquinone, 2-methyl-benzoquinone, 2,6-dimethyl-benzoquinone, 2,5-dimethyl-benzoquinone, and 2,3,5-trimethyl-benzoquinone (Rossi et al., 1986), γ-tocopherolquinone and δ-tocopherolquinone; isoflavones such as, but not limited to, catechin, daidzein, dicumarol, (−)epicatechin, flavopiridol, genistein, β-lapachone, myricetin and rotenone; and phenols such as, but not limited to, curcumin [1,7-bis(4-hydroxy-3-methoxyphenyl)-1,6-heptadiene-3,5-dione], yakuchinone A [1-(4'-hydroxy-3'-methoxyphenyl)-7-phenyl-3-heptanone], yakuchinone B [1-(4'-hydroxy-3'-methoxyphenyl)-7-phenyl-hept-1-en-3-one], (−) epigallocatechin-3-gallate, resveratrol (3, 5, 4'-trihydroxy-trans-stilbene), and γ- and δ-tocopherols, the precursors of γ- and δ-tocopherolquinones, respectively (Thornton et al., 1995). Other agents that form adducts or conjugates with GSH include, but are not limited to, arsenic trioxide, $As_2O_3$, that forms the transient adduct $As(GS)_3$ with GSH (Dai et al., 1999).

In still a further embodiment, the agent is an agent of the class (iii) above, that inhibits the human γ-glutamylcysteine synthetase (GCS or GCL) enzyme, the first and rate-limiting enzyme of GSH biosynthesis, thus lowering the rate at which GSH is synthesized. An illustrative example of such an inhibitor is buthionine sulfoximine (BSO), that selectively inhibits γ-GCL (Nicole et al., 1998, Schafer & Buettner, 2001).

In yet another embodiment of the invention, the agent responsible for the depletion of GSH is an agent of the class (iv) above, that inhibits/deactivates glutathione reductase (GR), the enzyme responsible for the conversion of GSSG to GSH, thereby preventing the recycling of GSSG to GSH. An example of such an inhibitor is N,N'-bis(2-chloroethyl)-N-nitrosourea, also known as carmustine or BCNU (Schafer & Buettner, 2001), and similar compounds such as 1-(2-chloroethyl)-3-(cyclohexyl)-1-nitrosourea (Babson and Reed, 1978).

Besides the agents mentioned above, it should be mentioned that certain conditions may also decrease the cellular GSH content such as radiation therapy, glucose deprivation (Lee et al., 1998), hyperthermia (Lord-Fontaine and Averill, 1999) and hypoxia (Araye et al, 1998), and methods employing one or more of the above agents and these conditions as complementary therapy are envisaged by the present invention.

In another aspect, the present invention comprises a method of treatment of a tumor which comprises administering to a subject bearing a tumor a synergistic combination of at least two agents, each agent belonging to one of the classes:

(א) an agent that oxidizes GSH to GSSG;

(ב) an agent that forms an adduct or conjugate with GSH;

(ג) an agent that inhibits the GCS enzyme; and (ד) an agent that inhibits the GR enzyme.

Based on the differences in kinetics and mechanisms of the various types of agents (i) to (iv), the combinations of the invention will provide varying degrees of synergy with respect to the ratio of $[GSH]^2/[GSSG]$, increasing E and maintaining the raised E for the 15 or more hours as defined.

The agents of the types (i) and (ii) are agents that interact 1:1 or 1:2 with GSH. Being known that the cellular concentration of GSH, [GSH], is in the order of 0.5-10 mM, it can be calculated that, in order to have a significant effect on E, the concentration of these agents of the types (i) and (ii) must be in the order of some hundreds of μMs. When one or more oxidizing agents of the type (i) are administered, E will rapidly rise as GSH is oxidized to GSSG, and rapidly fall back to its original value, as electrons are transferred back via the enzyme, glutathione reductase, GR, from NADPH. The maintenance of an elevated E for tens of hours requires continuous administration of the oxidizing agent(s), which could reach several grams daily. However, an agent that inhibits GR, would necessitate the de novo synthesis of GR in order to reduce GSSG to GSH and restore the original value of E to the cell. Relative to electron transfer in the oxidation of GSH, the de-novo synthesis of the protein GR is very slow, and the half-life of the elevated E could be many hours. This permits a low frequency of drug administration and, hence, a lower daily dose. Here, the actual contact time of the tissue to the agent could be minutes, whereas the effective contact time, which is the duration of the E above $E_{CCP}$, can be hours. The adduct formation with GSH is generally irreversible. For the cell to replace the GSH removed by the adduct formation would require de-novo synthesis of GSH or the relevant enzyme, which is slow.

By adding, however, a second agent that prevents GSH restoration by irreversibly inhibiting the glutathione reductase (GR), a key enzyme in redox metabolism of GSH (Cohen, 1988), such as carmustine, the GSSG cannot be reduced back to GSH. E will remain high until there is more de novo synthesis of GR. Relative to the rate of electron transfer, de novo protein synthesis is very slow; e.g. in the case of GR, it takes 12 hours to restore 50% of the activity of GR, 24 hours to restore 70% of the GR (Cohen, 1988). However, if only carmustine is present, the GR would be inhibited with 10 μM, within ½ hour (Cohen, 1988). The oxidation of GSH to GSSG will be slight as the cell's control system for E will tend to resist the change in E. Hence, E will increase only slowly with time. In contrast, the combination of an oxidizing agent, for example, disulfiram, with carmustine, will generate a rapid increase in E with a half-life of many hours, inducing apoptosis of all the cells in the cycle; this is a synergistic combination. In contrast, the agents of types (iii) and (iv) above interact with an enzyme (GCS or GR). The concentration of enzymes is much lower than [GSH], hence less agent is required to obtain an effect. Moreover, to restore the normal [GSH] requires de-novo synthesis of GCS or GR, an intrinsically slow process. Thus, a more effective synergy will result from a combination of an agent of class (i) or (ii) above with an agent of class (iii) or (iv) above.

Thus, in one preferred embodiment of the invention, the invention provides a method for the treatment of a tumor which comprises the administration to a subject in need of a pharmaceutically effective amount of a synergistic combination of a first agent selected from the group consisting of an agent that oxidizes GSH and an agent that forms an adduct or a conjugate with GSH, with a second agent selected from the group consisting of an agent that inhibits the GCS enzyme and an agent that inhibits the GR enzyme.

In one preferred embodiment, the invention provides a synergistic combination of an agent that oxidizes GSH, that can be any GSH-oxidizing agent, preferably any of those disclosed hereinabove in the specification, more preferably disulfiram, and an agent that inhibits the GCS enzyme, preferably BSO.

In another preferred embodiment, the invention provides a synergistic combination of an agent that oxidizes GSH, that can be any GSH-oxidizing agent, preferably any of those disclosed hereinabove in the specification, more preferably disulfiram, that decreases GSH and increases GSSG, and an agent that inhibits the GR enzyme, preferably carmustine, preventing restoration of GSH. This will result in a rapid increase in E, and this high E will be maintained for the many hours required for the de novo synthesis of GR, resulting in a synergistic effect.

In a further preferred embodiment, the invention provides a synergistic combination of an agent that forms an adduct or conjugate with GSH, that can be any adduct- or conjugate-forming agent, preferably any of those disclosed hereinabove in the specification, more preferably an agent selected from ethacrynic acid, a quinone or diethyl maleate, and an agent that inhibits the GCS enzyme, preferably BSO, but with the exclusion of the combination of $As_2O_3$ and BSO.

In another preferred embodiment, the invention provides a synergistic combination of an agent that forms an adduct or conjugate with GSH, that can be any adduct- or conjugate-forming agent, preferably any of those disclosed hereinabove in the specification, more preferably an agent selected from ethacrynic acid, a quinone or diethyl maleate, and an agent that inhibits the GR enzyme, preferably carmustine.

A yet further preferred embodiment of the invention is to combine an oxidizing agent, that will decrease E rapidly, with an adduct-forming agent, that will remove GSH permanently, requiring de novo synthesis of GSH and/or the relevant enzyme, an intrinsically slow process. As adduct formation of GSH requires de novo synthesis of more GSH, to restore what has been removed, adduct formation is longer lasting. Furthermore, the kinetics/mechanism of oxidation are not the same as adduct formation; oxidation generates GSSG, which, according to the Nernst equation, amplifies the increase in E (amplifies the increase in the ratio of $[GSSG]/[GSH]^2$ so that not only does the denominator decrease, but the numerator also increases). Thus, a combination of an agent that oxidizes GSH together with an agent that forms an adduct with GSH, provides a synergistic effect. This combination produces both a more rapid attainment of $E_{CCP}$, and maintains it over a longer period of time, than either single agent separately. This is because oxidation is an electron transfer process from which GSH can be rapidly restored, whereas the formation of an adduct is much slower and requires de novo synthesis of GSH and/or the relevant enzyme for replenishment.

According to still other preferred embodiment of the invention, it is envisaged to use two different pairs of agents, one pair from the GSH-oxidant class and another from the adduct-forming class, where one agent of each pair has an aliphatic side chain, and the other member of the same pair lacks an aliphatic side chain, to optimize access to different parts of the body. This might be especially applicable if the tumor is widespread, In yet another preferred embodiment, the invention provides a combination of at least one water-soluble agent of any of the classes (i) to (iv) with at least one lipid-soluble agent of any of the classes (i) to (iv). This enhances the chances that some of the agents gain access to different parts of the body characterized by different "solubility barriers". Thus, no matter where a particular agent is located or formed, for example, the stomach, or elsewhere in the body, there is a good chance that the agents will reach to the tumor. Of course, this solubility problem can also optionally be overcome if the agents are introduced directly into the tumor tissue, for example, by injection, for example into the prostate sac in the case of a prostate cancer.

In a further preferred embodiment of the present invention, the combination of two or more agents of any of the classes (i) to (iv) is used together with a standard chemotherapeutic agent such as melphalan, that attacks the DNA via alkylation or intercalation and hence kills proliferating cells. GSH detoxifies standard chemotherapeutic agents, such as melphalan (Dai et al., 1999). Hence, the $[GSH]^2/[GSSG]$-decreasing agents act as "sensitizing agents" which will enhance this standard chemotherapeutic agent attack on the DNA of the cell, raising their cytotoxicity to drug-resistant cells. Thus, the addition of a $[GSH]^2/[GSSG]$-decreasing (which is, in effect, an E-increasing agent), weakens the tumor cells selectively, so that a smaller concentration of a standard chemotherapeutic agent will be rendered more effective against tumor cells. The different embodiments of the invention as defined herein are expected to restore the sensitivity of cancer cells, that have become insensitive to the standard chemotherapeutic agent(s) and have developed multidrug-resistance, to cell death.

Regardless of the particular agent or procedure, or combination thereof, according to a preferred embodiment of the present invention, the intracellular redox potential of the malignant cells, E, is preferably increased beyond a critical value, $E_{CCP}$, to induce apoptosis. E can be increased passively by decreasing the free GSH content of the cell, for example, by inhibiting GSH synthesis. GSH can be decreased actively in various ways, for example, by introducing oxidizing agents (prooxidants) as defined above, which oxidize GSH to GSSG. Alternatively, agents that combine with GSH to form an adduct or a conjugate also increase E of the cell actively, and hence have the effect of oxidizing agents. These adduct-forming or conjugate-forming agents produce the same general effect as the introduction of an oxidizing agent, i.e. they decrease GSH and increase E.

Many of the standard chemotherapeutic agents are conventionally considered to be antioxidants. If they act as reducing agents that increase GSH, decrease GGSG and decrease E, they will permit the RB protein to remain or become phosphorylated, allowing cell proliferation. Thus, whereas antioxidants might prevent cancer, e.g. by scavenging/neutralizing reactive oxygen species, they will enhance the proliferation of cancer once it starts. Without being limited to a single hypothesis, the novel approach of the present invention applies the anti-proliferative effect of the dephosphorylated (hypophosphorylated) RB protein to halt the progress of the cell through its cycle by increasing E. This will be applicable for any cancer having an operational RB protein (pRB). And if the effect of redox is primarily on the transcription factors rather than on the pRB, the method should work even if pRB is not functional.

A preferred feature of the present invention is to "match" a single $[GSH]^2/[GSSG]$-decreasing agent to the location of the specific non-metastasizing tumor. For example, when the method of the invention is applied to a patient with a brain tumor, the $[GSH]^2/[GSSG]$-decreasing agent should preferably be a relatively small molecule to optimize its passage through the blood-brain barrier, e.g. dopamine as hydrogen peroxide precursor.

In another aspect, the present invention provides pharmaceutical compositions for use in the methods encompassed by the invention. The composition comprises a pharmaceutically acceptable carrier and a pharmaceutically effective amount of a $[GSH]^2/[GSSG]$-decreasing agent as defined hereinbefore or combinations thereof, to be preferably administered according to a protocol that achieves the goal of the present invention. Thus, a pharmaceutically effective dosage of a $[GSH]^2/[GSSG]$-decreasing agent is a quantity of a $[GSH]^2/[GSSG]$-decreasing agent or combinations thereof, packaged or administered such as to maintain continuously the E of the cancer cells at about −190 to −200 mV for a time, tau, that will result in cessation/retardation of the proliferation of a tumor and/or to cause regression of a tumor. The combined amounts of different classes of $[GSH]^2/[GSSG]$-decreasing agents which is pharmaceutically effective is a quantity of two or more such agents which, when combined and administered to maintain continuously the E of the cancer cell at about −190 to −200 mV for a time, tau retard the proliferation of a tumor and/or cause regression of a tumor. This time corresponds to 1-3 the cell cycle period and is within the range of from about 15 to about 72 hours, preferably from about 20 to about 60, more preferably from about 25 to about 50, still more preferably from about 30 to about 45 hours, these values depending on the type of tissue and the type and stage of the tumor.

As used herein, the term "pharmaceutically acceptable carrier" encompasses any of the standard pharmaceutical carriers. Such carriers are well known in the art and may include, but are in no way and are not intended to be limited to, any of the standard pharmaceutical carriers such as phosphate-buffered saline solutions, water, emulsions such as oil/water emulsion, suspensions, and various types of wetting agents. Typically, such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives, preservatives and the like, as well as other ingredients.

The pharmaceutical compositions for use according to the invention are formulated by well-known conventional methods. The compositions of this invention may include sterile solutions, tablets, coated tablets, capsules, pills, ointments, creams, lotions, gels, suppositories, pessaries, drops, liquids, sprays, powders, patches or any other means known in the art.

When a combination of two or more agents are used, a drug-delivery system embodying the present invention optionally and preferably comprises a pharmaceutically effective package having at least one, and preferably two, or three, or four or more separate dosage units of different $[GSH]^2/[GSSG]$-decreasing agents. As regards dosage, the $[GSH]^2/[GSSG]$-decreasing agent(s) is optionally and more preferably administered cumulatively in an amount of from about 0.01 g to about 1-8 grams per day. The administration of the compositions of this invention, which has to ensure the effective presence of the agent or agents, i.e. the maintenance of E above $E_{CCP}$, for a time, tau, may be effected by any of the well-known and suitable methods of administration, including, but not limited to, intravenous, intramuscular, intravesical, intraperitoneal, topical, transdermal (for example, using a patch containing one or more agents according to the invention), transmucosal, subcutaneous, rectal, vaginal, ophthalmic, pulmonary (inhalation), nasal, oral and buccal administration, by inhalation or insufflation (via the nose or mouth), administration as a coating to a medical device (e.g. a stent) and slow-release formulations (or packaging).

When a second $[GSH]^2/[GSSG]$-decreasing agent is administered in conjunction with a first $[GSH]^2/[GSSG]$-decreasing agent, this means that the second agent is administered prior to, at the same time as, or subsequent to, administration of the first agent, preferably as prescribed by a treatment schedule/protocol. Similarly, when a third $[GSH]^2/[GSSG]$-decreasing agent is administered in conjunction with a first and a second agents, this means that the third agent is administered prior to, at the same time as, or subsequent to, administration of the first and second agents. Similarly, when a fourth $[GSH]^2/[GSSG]$-decreasing agent is administered in conjunction with a first, second and third agents, this means that the fourth agent is administered prior to, at the same time as, or subsequent to, administration of the first, second and third agents. It is also envisaged that 5 or more $[GSH]^2/[GSSG]$-decreasing agents may optionally be used in an embodiment of this invention.

Without going to the very fine details, it is envisaged by the present invention that whenever a combination of two or more $[GSH]^2/[GSSG]$-decreasing agents are used, the agents should belong to at least two of the classes of agents (i) to (iv) defined above, preferably at least one agent is from the class (i) or (ii) and the at least another agent is from the class (iii) or (iv), and each of such agent is chosen from the groups of compounds defined above for each such class (i) to (iv) or from other known compounds or to be discovered in the future that comply with the definitions of the classes (i) to (iv).

It is also envisaged by the present invention to combine the treatment with at least one $[GSH]^2/[GSSG]$-decreasing agent together with a non-drug treatment including glucose deprivation, hypoxia, hyperthermia or radiation.

These and other embodiments will be illustrated by the following illustrative and non-limitative Examples.

EXAMPLES

Material and Methods (i) Animals tumor model—the tumor type will determine the choice of species, strain, sex, age of the animals for the experiments, e.g. mice, rats, rabbits, dogs, cats. For most models, mice and rat models are available. About 40 to 100 animals will be used in each experiment (half test animals, half controls).

(ii) Establishment of tumor models—human xenograft tumor models obtained by injecting human cancer cell lines into athymic nude mice, or murine tumor models obtained by introducing syngeneic cancer cell lines that generate tumors in mice with an intact immune system, can be used in the experiments. Also transgenic mice expressing an oncogene and knockout mice may be used.

Many tumor cell lines from human and rodent origin are available such as the human colorectal adenocarcinoma HT-29 and SW-480 cell lines, the human breast adenocarcinoma BT-20 cell line, the human prostate adenocarcinoma PC-3 cell line, the human ovary adenocarcinoma OVCAR-3 cell line, the murine Lewis lung carcinoma cell line, the murine B-16 melanoma cell line, and the rat pancreatic AR42J tumor line. The cells should be free of human as well as murine pathogens.

Tumors are propagated in vitro and in vivo. For cells maintained in vitro, tumors are generated by injecting precisely determined numbers of cells into mice. For tumors which are best propagated in vivo, tumor fragments from donor mice are implanted into small numbers of mice for maintenance, or larger numbers of mice for study initiation.

The study may include colon cancer cell lines. The HT-29 cell line is a human colorectal adenocarcinoma, which when injected into nude mice is tumorigenic, with a take rate of approximately 80-90%. Tumors reach a mean target window size of 100-200 mg in 4-6 days and a mean tumor size of 1000 mg in 35-40 days.

The study may include the rat pancreatic tumor line, AR42J, that is propagated in vivo. Typically, tumors are sterilely collected from donor mice when they reach approximately 1000 mg, and a 10 mg tumor fragment is implanted subcutaneously into donor athymic nude mice. This tumor line is tumorigenic in approximately 70-80% of mice implanted and reaches a mean target window size of 100-200 mg in 20-25 days. A mean size of 800-900 mg is reached in approximately 40 days.

(iii) Administration of the agent(s) according to the invention—

Routes of administration may include subcutaneous (SC), intraperitoneal (IP), intravenous (IV), intramuscular (IM), intradermal (ID) and oral (PO).

(iv) Follow-up of the experiment and analysis of the results—Tumor size and body weights are taken over the course of the study and morbidity and mortality are recorded. If the tumor fails to grow, this is an indication of cell-cycle arrest, and if the tumor shrinks, this is an indication of apoptosis. In addition, tumor histology (apoptosis, necrosis, degree of mitosis), testing of metastases and laboratory tests (chemistry and hematology) are carried out.

Example 1

Tumor Treatment with One GSH-Decreasing Agent Alone or with a Standard Chemotherapeutic Agent A single GSH-decreasing agent selected from those described in the specification such as BSO, disulfiram or carmustine, is administered to groups of test animals at different concentrations: 1-50 µM for BSO and disulfiram, and 0.1-5 µM for carmustine, during various periods of time: for 15, 30 and 60 hours. The tests are repeated in groups of animals with the addition of melphalan (0.1-5 µM).

Example 2

Tumor Treatment with Synergistic Combination of Disulfiram and BSO

Disulfiram, an agent that oxidizes GSH, is administered in dosages of 0.1-50 mg to a tumor-bearing mouse. The tumor is checked and the minimum dosage at which the tumor will stop growing and begins to regress (minimum effective dose=MED) is determined. This dosage is called $D_{01}$.

The treatment is repeated with BSO, an agent that inhibits GCS enzyme, in doses of 0.1-50 mg, and the MED thus determined is called $D_{02}$.

The treatment is repeated with both disulfiram and BSO, using a dosage of 50% of the dosage $D_{01}$, as determined for disulfiram, and 20%, 30%, and 40% of $D_{02}$ of BSO, and the minimum effective dose of BSO at which the tumor will stop growing and begin to regress is determined. The minimum dose is expected to be dependent on the change in redox potential, $\Delta E$, required to stop tumor growth or cause regression. If that difference is 10 mV, the dosage of $C_2$ is expected to be about 35% of $D_{02}$; if $\Delta E=20$ mV, then the dosage is expected to be about 25% of $D_{02}$, and if $\Delta E=30$ mV, the dosage is expected to be about 20% of $D_{02}$.

Example 3

Tumor Treatment with Synergistic Combination of Disulfiram and Carmustine

Disulfiram is administered to a group of tumor-bearing mice as described in Example 2 above.

The treatment is repeated with BCNU (carmustine), an agent that inhibits the GR enzyme, in dosages of 0.01-0.1 mg to a tumor-bearing mouse. The tumor is checked and the minimum dosage at which the tumor will stop growing and begins to regress (minimum effective dose=MED) is determined. This dosage is called $D_{02}$.

The treatment is repeated with both disulfiram and BCNU, using a dosage of 50% of the dosage $D_{01}$, as determined for disulfiram, and 10%, 25%, and 40% of $D_{02}$ of BCNU. Determine the minimum effective dose of BCNU at which the tumor will stop growing and begin to regress. The minimum dose is expected to be dependent on the change in redox potential, $\Delta E$, required to stop tumor growth or cause regression.

Some pharmacological aspects of the agents BSO, disulfiram and carmustine are presented below in Table 1.

TABLE 1

Pharmacological aspects of BSO, Disulfiram & Carmustine

| Parameter | Buthionine sulfoximine (BSO) | Disulfiram ((DSF | Carmustine ((BCNU |
|---|---|---|---|
| Usual dosage | 1.5 g/sq · m to 13.1 g/sq · m [Bailey] | Initially 500 mg/day for 1-2 weeks, followed by a maintenance dose of 125-500 mg/day | mg/day 100 |
| Normal dosage protocol | Continuous IV infusion for 48 hours | 1-2 weeks; then half the dose | days 3-2 |

TABLE 1-continued

Pharmacological aspects of BSO, Disulfiram & Carmustine

| Parameter | Buthionine sulfoximine (BSO) | Disulfiram ((DSF) | Carmustine ((BCNU |
|---|---|---|---|
| Action on GSH and GSSG | Selectively binds to the active site of gamma-glutamyl-cysteine synthetase, the rate limiting step in GSH synthesis → inhibition of GSH synthesis | Oxidizes GSH [Cen] Diethyldithio-carbamate (DDC), an active metabolite of disulfiram, affects glutathione reductase (GR) | Inhibits glutathione reductase (GR) [Cohen & Duval], leading to depletion of GSH |
| Apoptosis Concentration | Enhancement [Kito] 10-25 microM | Induction 10 microM [Cen] | Induction 50 ng/ml [Cohen & Duval] |
| Solubility [Merck] | Soluble | 0.02 g/100 ml | 4 mg/liter |
| Toxicity: | 9.6 g/kg (mice) → transient leukopenia, renal tubular necrosis (in association with melphelan) [Smith] occasional nausea/vomiting [Bailey] | 3 g (adults) | |
| $LD_{50}$ [Merck] | | 8.6 g/kg (rats) | 25-30 mg/kg (mice/rats) |

Example 4

This example describes treatment with three agents, namely, BSO (B), carmustine/BCNU (C) and disulfiram (D).

| Compound | Effective Concentration in vitro (microM) | Experimental Range (microM) | Solubility (microM) | Toxicity (microM) |
|---|---|---|---|---|
| Disulfiram (D) | 10 | 1-100 | 2,000 | 10,000 |
| Carmustine (C) | 0.05 | 0.01-1 | 40 | 14 |
| BSO (B) | 100 | 10-1,000 | soluble | 10,000 |

The animals (120 mice—5 groups of 20 test animals, 20 controls) are treated either with a sole agent B, C or D, or with a combination of B+D, or with a combination C+D, in concentrations varying in the experimental range described above. The tumor may be a xenograft prostate cancer under skin or melanoma induced on foot, or any other suitable animal tumor model. The agents are dissolved in drinking water and administered to the test mice (15 ml/kg) (optionally with a taste improver both to control and test) continuously for 2 days. Alternatively, the skin of the animals is bathed continuously for 2 days via a patch soaked in the water containing the three agents (Intradermal administration) and renewed periodically. In a third alternative, the three agents are administered for 24-48 hours by continuous infusion. Control mice receives plain drinking water.

In a first experiment, drinking water is provided to the test animals containing either B, C, or D separately, or a combination of B+D for one group, of C+D for a second group, and plain water for control. In all cases, the concentration of the agents is within the range listed above. The size of the tumors is measured every third day. The % survival is determined as a function of time. The size of the tumor decreases and the % survival increases for the test experiments, relative to the control. With the two combinations, the effect is synergistic.

Example 5

Synergy of GSH-Decreasing Agents

This example provides the theoretical basis for the synergy of the combinations of agents according to the invention.

The intracellular glutathione (GSH) concentration is presumed here to be controlled through several negative feedback loops. This description shows how GSH depleting agents act in conjunction with such a control system to lower [GSH], the concentration of GSH. The following control factors, which influence [GSH], are considered here:

1. Feedback inhibition on the gene encoding the rate-limiting enzyme in the biosynthesis of GSH. Gene control in mammals is known to be in general complex. But ultimately the gene is shut off when there is a sufficient amount of the product in the cell. In the case of GSH control, we assume the gene is normally ON and is turned OFF by a repressor. The repressor is either the GSH molecule itself, or a special repressor molecule, which the GSH molecule activates.

2. The first enzyme of a series of reactions is usually inhibited by a negative feedback effect of the final product of that pathway. In the case of GSH synthesis, the rate-limiting enzyme may be inhibited by the GSH molecule itself.

3. The cell continually degrades the enzyme, with a time constant consistent with the rate at which [GSH] must change to respond to the changes inherent in the cell cycle.

4. The concentration of the biosynthetic precursor of GSH plays a role in setting the concentration [GSH].

5. Oxidation of GSH to GSSG plays a role in lowering [GSH] while it increases [GSSG], causing the intercellular redox potential E to rise associated parameters.

In this analysis, we leave the above factors in parametric form, and from the expression derived for the steady-state value of [GSH], it is possible to design experiments to determine some of their values. The above effects can also be influenced by external agents introduced into the cell. We introduce parameters denoting the concentrations of such agents to examine the possible effects of such agents and their functional dependence on their concentrations.

Taking account of these factors leads to a nonlinear second-order differential equation in [GSH] as a function of time. Here, we shall compute the steady-state value of [GSH], and I shall not consider the solution of the differential equation at this time.

Feedback Inhibition of the Gene

We assume the GSH molecule represses the gene that encodes the rate-limiting enzyme in the biosynthesis of GSH and that, once repressed, the repression lasts for some time interval τ. Let p denote the probability that a particular GSH molecule will execute repression in time τ. Then the probability that a particular GSH molecule will not execute repression in time τ is (1−p). Let the number of GSH molecules in the cell be denoted by N. Then the probability that none of them repress in time τ is given by $(1-p)^N$, and this is just the probability that the gene will be ON at any time. It is reasonable to say that p<<1, so that the probability of the gene being ON is very closely $$P=\exp(-pN). \quad (1)$$

We can write N as $$N=N_A vx, \quad (2)$$

where $N_A$ is Avogadro's number in mole$^{-1}$, v is the cell volume in liters, and x is the GSH concentration in moles per liter. To get a feel for some of the numbers involved, note that the cell volume is of the order of $10^{-12}$ liters, and [GSH] in the cell is of the order of $10^{-3}$ moles/liter. We can therefore say that N is of the order of $6\times10^8$. Then the exponent in (1) can be written as $$pN = kx, \qquad (3)$$

where $k=pvN_A$, in units of liters/mole, so that (1) can be written as $$P = \exp(-kx). \qquad (4)$$

When the gene is ON, the corresponding enzyme is synthesized. The enzyme molecules, in turn, catalyze the synthesis of GSH. The transcription of the gene will lead to a rate of production of enzyme molecules. Each enzyme will continually catalyze the reactions synthesizing GSH until the enzyme is degraded. Thus, the synthesis of one enzyme molecule will cause a fixed increase in the number of GSH molecules.

The rate of production of the enzyme will be some value, which we shall denote by W, when the gene is ON, and zero when the gene is OFF. We shall denote the enzyme concentration by z in units of moles/liter. The average rate of enzyme production is W times the probability that the gene is ON, or $$dz/dt = W\exp(-kx). \qquad (5)$$

The value of W will depend upon the cell-cycle phase: It will be larger in S, $G_2$, and M, and will be smaller in $G_0$ and $G_1$ (Yamauchi & Bloom 1997).

The enzyme molecules are continually degraded, and we assume the rate of degradation of the enzyme to be proportional to its concentration. We can write the rate of removal of the enzyme as $k_z z$, where $k_z$ is a constant of proportionality and has units of sec$^{-1}$.

Use of an Enzyme-Removal Agent

If an agent is introduced into the cell that effectively removes the enzyme, then this removal will also be proportional to the enzyme concentration through a constant of proportionality $c_1$, also having units of sec$^{-1}$. Then the resulting net rate of increase of the enzyme is given by $$dz/dt = W\exp(-kx) - (k_z + c_1)z. \qquad (6)$$

Michaelis-Menton Model of Enzyme Activity

Here we use the Michaelis-Menton model to derive the equation of the rate of increase of [GSH]. We shall take account of the feedback inhibition of the GSH molecule on the enzyme activity, and we shall use the following notation:

x=[GSH]
z=concentration of total enzyme
$z_a$=concentration of available enzyme
$z_i$=concentration of inhibited enzyme
s=concentration of the biosynthetic precursor to GSH=[S]
[ZS]=concentration of the enzyme-substrate complex.

The enzyme Z and the substrate S first combine to form the enzyme-substrate complex ZS, and then the complex breaks apart to yield the product GSH, recovering the enzyme Z. Thus $$Z+S \rightarrow ZS, \text{ with rate constant } k_1, \qquad (8)$$

$$Z+S \leftarrow ZS, \text{ with rate constant } k_2, \text{ and} \qquad (9)$$

$$ZS \rightarrow Z+GSH, \text{ with rate constant } k_3, \qquad (10)$$

where $k_1$ has units of (liter mole$^{-1}$ sec$^{-1}$), and $k_2$ and $k_3$ have units of sec$^{-1}$.

From (10) it is evident that the rate of formation of GSH is proportional to [ZS] as $$\frac{dx}{dt} = k_3[ZS]. \qquad (11)$$

The enzyme Z in (8)-(10) is the available enzyme, whose concentration is $z_a$. The rate of formation of the complex ZS is proportional to the product of the concentrations [Z] and [S] with the proportionality constant $k_1$ $$\text{Rate of formation of } ZS = k_1[Z][S] = k_1 z_a s, \qquad (12)$$

and its rate of breakdown is $$\text{Rate of breakdown of } ZS = (k_2+k_3)[ZS]. \qquad (13)$$

In steady state, the concentration [ZS] is constant, so that its rate of formation is equal to its rate of breakdown, $$k_1 z_a s = (k_2+k_3)[ZS], \qquad (14)$$

from which we can write $$[ZS] = \frac{z_a s}{(k_2+k_3)/k_1}, \qquad (15)$$

and letting $$K_M = \frac{k_2+k_3}{k_1}, \qquad (16)$$

which is known as the Michaelis-Menton constant, we can write (15) as $$[ZS] = \frac{z_a s}{K_M}. \qquad (17)$$

Now $z_a$ can be written as $$z_a = z - z_i - [ZS]. \qquad (18)$$

Inhibition of the enzyme can be of two types: competitive and noncompetitive. We shall first treat the competitive type, since inhibition by the product of the reaction is usually of that type. For this type, the inhibited portion of the total enzyme, $z_i$, is proportional to the product of the concentration of the available enzyme $z_a$ and of [GSH], which we have denoted by x. Thus $$z_i = z_a x/k_i, \qquad (19)$$

where $k_i$ is a constant of proportionality having units of moles/liter, and is known as the dissociation constant of the enzyme-inhibitor complex. Then putting (17) and (19) in (18), we get $$z_a = z - \frac{z_a x}{k_i} - \frac{z_a s}{K_M}. \qquad (20)$$

Solving (20) for $z_a$ gives $$z_a = \frac{z}{1 + \frac{x}{k_i} + \frac{s}{K_M}}. \tag{21}$$

From (11) and (17) we have $$\frac{dx}{dt} = \frac{k_3 s z_a}{K_M}, \tag{22}$$

and from (21) we get, for competitive inhibition, $$\frac{dx}{dt} = \frac{k_3 s z}{K_M\left(1 + \frac{x}{k_i}\right) + s}. \tag{23}$$

For noncompetitive inhibition, the inhibited portion of the enzyme $z_{in}$ is proportional to the total enzyme minus the inhibited portion, instead of to the available enzyme as in the case of competitive inhibition. Thus, $$z_{in} = \frac{(z - z_{in})x}{k_{in}}, \tag{24}$$

where $k_{in}$ is the appropriate dissociation constant. Solving for $z_{in}$ in (24) gives $$z_{in} = \frac{zx}{k_{in} + x}. \tag{25}$$

From (17)

$$[ZS] = \frac{(z - z_{in} - [ZS])s}{K_M}. \tag{26}$$

Solving (26) for [ZS] yields $$[ZS] = \frac{(z - z_{in})s}{K_M + s}. \tag{27}$$

Using (25) in (27) yields $$[ZS] = \frac{zs}{(K_M + s)\left(1 + \frac{x}{k_{in}}\right)}. \tag{28}$$

From (11) and (28), we get, for noncompetitive inhibition, $$\frac{dx}{dt} = \frac{k_3 s z}{(K_M + s)\left(1 + \frac{x}{k_{in}}\right)}. \tag{29}$$

Use of an Enzyme-Inhibiting Agent

Competitive Inhibition

If one were to introduce an enzyme inhibitor into the cell, it would increase the inhibition beyond that effected by the GSH molecule itself. The effect of the inhibitor would be proportional to the available enzyme and would be a measure of the fraction of that enzyme that is effectively removed. Then, for a competitive inhibitor, the inhibited fraction of the enzyme can be written as $$z_i = z_a\left(\frac{x}{k_i} + c_2\right), \tag{30}$$

where $c_2$ is dimensionless. Using (30) and (17) in (18), we get $$z_a = z - z_a\left(\frac{x}{k_i} + c_2\right) - \frac{z_a s}{K_M}, \tag{31}$$

which yields $$z_a = \frac{z}{1 + \frac{x}{k_i} + c_2 + \frac{s}{K_M}}. \tag{32}$$

From (22) and (32) we get $$\frac{dx}{dt} = \frac{k_3 s}{K_M} \frac{z}{1 + \frac{x}{k_i} + c_2 + \frac{s}{K_M}}, \tag{33}$$

or, the rate of increase of [GSH], for competitive inhibition, is given by $$\frac{dx}{dt} = \frac{k_3 s z}{K_M\left(1 + \frac{x}{k_i} + c_2\right) + s}. \tag{34}$$

Noncompetetive Inhibition

If we use a noncompetitive inhibiting agent, we get the expression for the rate of increase of [GSH] by inserting in (29) a term $c_4$ denoting the concentration of the agent as $$\frac{dx}{dt} = \frac{k_3 s z}{(K_M + s)\left(1 + \frac{x}{k_{in}} + c_4\right)}. \tag{34a}$$

GSH-Removal Agent

But GSH is also removed from the cell in the normal course of events, and the rate of removal is again proportional to the concentration x. Let $k_u$ be the proportionality constant for the natural removal, and let $c_3$ (having units of $\sec^{-1}$) be that for the deliberate removal by an agent introduced into the cell. Thus the equation for the rate of GSH increase in the cell is $$\frac{dx}{dt} = \frac{k_3 s z}{K_M\left(1 + \frac{x}{k_i} + c_2\right) + s} - (k_u + c_3)x. \quad (35)$$

The rate of increase of the enzyme concentration z is given by (6), $$dz/dt = W\exp(-kx) - (k_z + c_1)z. \quad (6)$$

In steady state (if there is one), the derivatives in (6) and (35) are zero, and the steady-state value, $x_{ss}$, can be obtained by setting the derivatives to zero in (35) and (6). From (6) we get $$z_{ss} = \frac{W}{k_z + c_1}\exp(-k_0 x_{ss}), \quad (36)$$

and from (35), $$z_{ss} = \frac{k_u + c_3}{k_3 s}\left[K_M\left(1 + \frac{x_{ss}}{k_i} + c_2\right) + s\right]x_{ss}. \quad (37)$$

Equating the right-hand sides of (36) and (37) yields an equation for the steady-state concentration of GSH, $$\exp(-k_0 x_{ss}) = \frac{(k_u + c_3)(k_z + c_1)}{k_3 W s}\left[\frac{K_M}{k_i}x_{ss}^2 + (K_M\{1 + c_2\} + s)x_{ss}\right]. \quad (38)$$

The solution of (38) for $x_{ss}$ gives the steady-state value of [GSH]. To see how $x_{ss}$ depends on the parameters in (38), we shall rewrite (38), letting $$y = k_0 x_{ss}. \quad (39)$$

Then (38) can be written as $$\exp(-y) = Ay^2 + By, \quad (40)$$

where $$A = \frac{K_M(k_u + c_3)(k_z + c_1)}{k_0^2 k_i k_3 W s}, \text{ and} \quad (41)$$

$$B = \frac{(k_u + c_3)(k_z + c_1)}{k_0 k_3 W s}[K_M(c_2 + 1) + s]. \quad (42)$$

One can see from the form of (40) that y is a monotonic decreasing function of both A and B. This can most easily be seen by writing the partial derivatives of y with respect to A and B, $$\frac{\partial y}{\partial A} = \frac{-y^2}{e^{-y} + 2A + B} \text{ and} \quad (43)$$

$$\frac{\partial y}{\partial B} = \frac{-y}{e^{-y} + 2Ay}. \quad (44)$$

Note that since y, A, and B are all positive, (43) and (44) show that y is a monotonic decreasing function of both A and B. This means that the larger is A or B, the smaller is y. Thus, larger values of the agent concentrations, $c_1$, $c_2$, or $c_3$, the smaller the steady-state value of GSH, which is denoted by $x_{ss}$ in (38). Similarly, the larger s, the smaller $x_{ss}$.

We can simplify the appearance of A and B in (41) and (42) by defining $$A_0 = \frac{k_u k_z}{k_0^2 k_1 k_3 W}, \text{ and} \quad (45)$$

$$B_0 = \frac{k_u k_z}{k_0 k_3 W}, \quad (46)$$

and defining normalized concentrations, $C_1$ and $C_3$, of agents as $$C_1 = c_1/k_z \quad (47)$$

$$C_3 = c_3/k_u \quad (48)$$

and a normalized concentration of GSH precursor as $$S = s/K_M. \quad (49)$$

Then we can write A and B as $$A = A_0\frac{(1 + C_1)(1 + C_3)}{S} \text{ and} \quad (50)$$

$$B = B_0\frac{(1 + C_1)(1 + C_3)(1 + c_2 + S)}{S} \quad (51)$$

Note in (38) that the parameters $C_1$, $c_2$, and $C_3$ are under therapeutic control. And as has just been shown, as the value of any of these parameters is increased, $x_{ss}$ decreases. Note, moreover the synergistic relationship among them. Since each contributes to the value of a factor in the denominator, their effects can multiply, producing synergy.

The effects of $C_1$, and $c_2$ in this regard are clear. The effect of $C_3$, however depends upon the substrate concentration, S. The larger is S, the less effect $C_3$ can produce. Indeed, as S→∞, the effect of the term in the square brackets of denominator of the right-hand side of (51) disappears. Therefore, to enhance the effect of $C_3$ in lowering [GSH], one should try to lower the concentration S of the precursor to GSH. To the extent that it can be done, the lowering of S would itself contribute to lowering [GSH].

We thus see from (50) and (51) that there may be four different kinds of agents for lowering [GSH] that, when administered together, will have a synergistic effect. These are:

1. An agent to effectively remove the rate-limiting enzyme in the biosynthesis of GSH ($C_1$)
2. An agent to inhibit the activity of the rate-limiting enzyme ($c_2$)
3. An agent to effectively remove GSH($C_3$)
4. An agent to reduce the concentration of the precursor of GSH.

Figure 2:
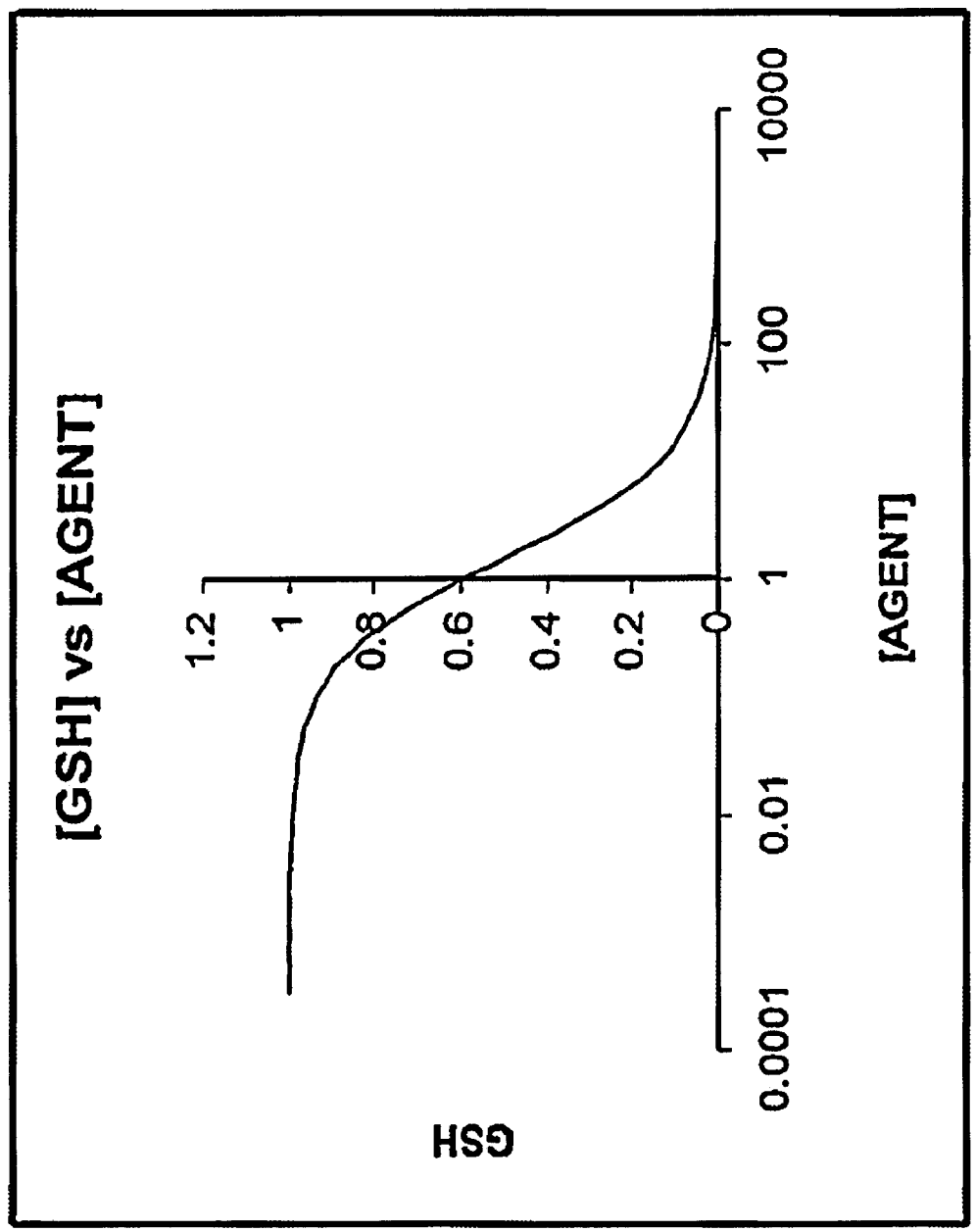
FIG. 2 is a normalized plot of [GSH] versus C1.

Although the above concentrations are normalized and are not given in absolute values, nevertheless their absolute values can be established through cell-culture experiments. Thus, various concentrations of each kind of agent can be administered and the [GSH] measured. A plot of [GSH] versus agent concentration can be experimentally established to determine the absolute scale of the agent and GSH concentrations. A normalized plot of [GSH] versus C1 is shown in FIG. 2. Experimental measurements will establish the scale on both the x and the y axes.

REFERENCES

Araya R, Uehara T, Nomura Y. (1998) "Hypoxia induces apoptosis in human neuroblastoma SK-N-MC cells by caspase activation accompanying cytochrome c release from mitochondria." *FEBS Lett* 439:168-72

Babson, J R. and Reed, D J (1978) "Inactivation of glutathione reductase by 2-chloroethyl nitrosourea-derived isocyanates." *Biochem. Biophys. Res. Commun.* 83: 745-762.

Bailey H H, Mulcahy R T, Tutsch K D, Arzoomanian R Z, Alberti D, Tombes M B, Wilding G, Pomplun M, Spriggs D R. Phase I clinical trial of intravenous L-buthionine sulfoximine and melphalan: an attempt at modulation of glutathione. *Journal of Clinical Oncology* 1994; 12: 194-205.

Cen D, Gonzalez R I, Buckmeier J A, Kahlon R S, Tohidian N B, Meyskens F L Jr. (2002) "Disulfiram induces apoptosis in human melanoma cells: a redox-related process." *Molec Cancer Ther* 1: 197-204.

Cohen M B, Duval D L. (1988) "Characterization of the inhibition of glutathione reductase and the recovery of enzyme activity in exponentially growing murine leukemia (L1210) cells treated with 1,3-bis(2-chloroethyl)-1-nitrosourea." *Biochem Pharm* 37:3317-3320.

Cornwell D G, Jones K H, Jiang Z, Lantry L E, Southwell-Keely P, Kohar I, Thornton D E (1998) "Cytotoxicity of tocopherols and their quinones in drug-sensitive and multidrug-resistant leukemia cells." *Lipids* 33:295-301.

Dai J, Weinberg R S, Waxman S, Jing Y. (1999) "Malignant cells can be sensitized to undergo growth inhibition and apoptosis by arsenic trioxide through modulation of the glutathione redox system." *Blood* 93: 268-77.

Duval D L, Sieg D J, Billings R E. (1995) "Regulation of hepatic nitric oxide synthase by reactive oxygen intermediates and glutathione". *Arch Biochem Biophys* 316:699-706.

Esterbauer H, Schaur R J, Zollner H. (1991) "Chemistry and biochemistry of 4-hydroxynonenal, malonaldehyde and related aldehydes." *Free Radic Biol Med* 11: 81-128.

Gottlieb T M, Oren M. (1996) "p53 in growth control and neoplasia." *Biochim Biophys Acta* 1287: 77-102.

Hoffman A, Spetner L M, Burke M. (2001) "Cessation of cell proliferation by adjustment of cell redox potential." *J Theoret Biol* 211:403-7.

Hutter D E, Till B G, Greene J J. (1997) "Redox state changes in density-dependent regulation of proliferation." *Exp Cell Res* 232:435-438.

Kang C D, Jang J H, Kim K W, Lee H J, Jeong C S, Kim C M, Kim S H, Chung B S. (1998) "Activation of c-jun N-terminal kinase/stress-activated protein kinase and the decreased ratio of Bcl-2 to Bax are associated with the auto-oxidized dopamine-induced apoptosis in PC12 cells." *Neurosci Lett* 256:37-40.

Kinscherf R, Deigner H P, Usinger C, Pill J, Wagner M, Kamencic H, Hou D, Chen M, Schmiedt W, Schrader M, Kovacs G, Kato K, Metz J. (1997) "Induction of mitochondrial manganese superoxide dismutase in macrophages by oxidized LDL: its relevance in atherosclerosis of humans and heritable hyperlipidemic rabbits." *FASEB J* 11:1317-28.

Kito M, Akao Y, Ohishi N, Yagi K, Nozawa Y. Arsenic trioxide-induced apoptosis and its enhancement by buthionine sulfoximine in hepatocellular carcinoma cell lines. *Biochem Biophys Res Commun.* 2002; 291:861-867.

Lahusen T, De Siervi A, Kunick C, Senderowicz A M (2003) "Alsterpaullone, a novel cyclin-dependent kinase inhibitor, induces apoptosis by activation of caspase-9 due to perturbation in mitochondrial membrane potential." *Molec Carcinogen* 36:183-194.

Lee Y J, Galoforo S S, Berns C M, Chen J C, Davis B H, Sim J E, Corry P M, Spitz D R. (1998) "Glucose deprivation-induced cytotoxicity and alterations in mitogen-activated protein kinase activation are mediated by oxidative stress in multidrug-resistant human breast carcinoma cells". *J Biol Chem* 273: 5294-9.

Li Y, Sun X, LaMont J T, Pardee A B, Li C J. (2003) "Selective killing of cancer cells by beta-lapachone: direct checkpoint activation as a strategy against cancer." *Proc Natl Acad Sci USA* 100:2674-8.

Li C J, Li Y Z, Pinto A V, Pardee A B. (1999) "Potent inhibition of tumor survival in vivo by beta-lapachone plus taxol: combining drugs imposes different artificial checkpoints." *Proc Natl Acad Sci USA.* 96:13369-74.

Lizard G, Gueldry S, Sordet O, Monier S, Athias A, Miguet C, Bessede G, Lemaire S, Solary E, Gambert P. (1998) "Glutathione is implied in the control of 7-ketocholesterol-induced apoptosis, which is associated with radical oxygen species production." *FASEB J.* 12: 1651

Lord-Fontaine S, Averill D A. (1999) "Enhancement of cytotoxicity of hydrogen peroxide by hyperthermia in chinese hamster ovary cells: role of antioxidant defenses." *Arch Biochem Biophys* 363:283-95.

Merck Index 11th edition, Rahway N.J., USA, 1989

Nicole A, Santiard-Baron D, Ceballos-Picot I. (1998) "Direct evidence for glutathione as mediator of apoptosis in neuronal cells." *Biomed Pharmacother* 52: 349-55.

Paschka A G, Butler R, Young C Y. (1998) "Induction of apoptosis in prostate cancer cell lines by the green tea component, (-)-epigallocatechin-3-gallate." *Cancer Lett* 130:1-7.

Ramachandran C, You W. (1999) "Differential sensitivity of human mammary epithelial and breast carcinoma cell lines to curcumin." *Breast Cancer Res Treat* 54:269-78.

Rimpler M M, Rauen U, Schmidt T, Moroy T, de Groot H. (1999) "Protection against hydrogen peroxide cytotoxicity in rat-1 fibroblasts provided by the oncoprotein Bcl-2: maintenance of calcium homoeostasis is secondary to the effect of Bcl-2 on cellular glutathione." *Biochem J* 340(Pt 1):291-7.

Rossi L, Moore G A, Orrenius S, O'Brien P J. (1986) "Quinone toxicity in hepatocytes without oxidative stress." *Arch Biochem Biophys* 251: 25-35.

Rudra P K, Krokan H E. (1999) "Acrolein cytotoxicity and glutathione depletion in n-3 fatty acid sensitive- and resistant human tumor cells." *Anticancer Res* 19: 461-9.

Schafer F Q, Buettner G R. (2001) "Redox environment of the cell as viewed through the redox state of the glutathione disulfide/glutathione couple." *Free Rad Biol Med* 30:1191-212.

Sen C K, Sashwati R, Packer L. (1999) "Fas mediated apoptosis of human Jurkat T-cells: intracellular events and potentiation by redox-active alpha-lipoic acid." *Cell Death Differentiation* 6:481-91.

Smaaland R, Svardal A M, Lote K, Ueland M, Laerum O D. (1991) "Glutathione content in human bone marrow and circadian stage relation to DNA synthesis." *J Natl Cancer Inst* 83:1092-8.

Smith A C, Liao J T, Page J G, Wientjes M G, Grieshaber C K. Pharmacokinetics of buthionine sulfoximine (NSC 326231) and its effect on melphalan-induced toxicity in mice. *Cancer Research,* 1989; 49:5385-5391.

Tamrakar, S, Rubin E, Ludlow J W (2000) "Role of pRB dephosphorylation in cell cycle regulation" *Frontiers in Bioscience* 5: D121-137

Thornton D E, Jones K H, Jiang Z, Zhang H, Liu G, Cornwell D G. (1995) "Antioxidant and cytotoxic tocopheryl quinones in normal and cancer cells." *Free Radic Biol Med* 18:963-76.

Wullner U, Seyfried J, Groscurth P, Beinroth S, Winter S, Gleichmann M, Heneka M, Loschmann P, Schulz J B, Weller M, Klockgether T. (1999) "Glutathione depletion and neuronal cell death: the role of reactive oxygen intermediates and mitochondrial function." *Brain Research* 826: 53-62.

Yamauchi A, Bloom E T. (1997) "Control of cell cycle progression in human natural killer cells through redox regulation of expression and phosphorylation of retinoblastoma gene product protein" *Blood* 89: 4092-409.

Zetterberg A and Larsson O, (1985) "Kinetic analysis of regulatory events in G1 leading to proliferation or quiescence of Swiss 3T3 cells." *Proc Natl Acad Sci USA* 82:5365-9.

Zetterberg A and Larsson O. (1995) "Cell cycle progression and cell growth in mammalian cells", in *Frontiers in Molecular Biology: Cell Cycle Control,* Ed. by Hutchings C and Glover D M, p 2066, Oxford University Press, Oxford, UK.

Zetterberg A, Larsson O, Wiman K G (1995) "What is the restriction point?" *Curr Opinion in Cell Biology* 7:835-42.

Zhou J R, Gugger E T, Tanaka T, Guo Y, Blackburn G L, Clinton S K. (1999) "Soybean phytochemicals inhibit the growth of transplantable human prostate carcinoma and tumor angiogenesis in mice." *J Nutrition* 129:1628-35.

The invention claimed is:

1. A method of treating a patient having a tumor comprising malignant cancer cells having an operative retinoblastoma (RB) protein, by dephosphorylizing the RB protein in said cancer cells and continuously maintaining a dephosphorylated state of the RB in said cancer cells to induce apoptosis thereof, comprising the steps of:

administering to said patient having a tumor comprising malignant cancer cells having an operative retinoblastoma protein a pharmaceutically effective dosage of a drug to cause an increase in intracellular redox potential (E) and decrease in the $[GSH]^2/[GSSG]$ (wherein [GSH] is the concentration of glutathione and [GSSG] is the concentration of glutathione disulfide) ratio in the malignant cancer cells of said tumor, said drug comprising a combination of the two E-increasing agents disulfram and curcumin and the two enzyme deactivating agents bis-chloronitrosourea (BCNU) and buthionine sulfoximine (BSO);

said pharmaceutically effective dosage of said drug further comprising a plurality of separate dosage units of said drug administered in a cumulative amount of from 0.01-8 grams per day of said E-increasing agents as needed to continuously maintain said decreased [GSH] 2/[GSSG] ratio in the malignant cells and consequently continuously maintain said dephosphorylated state of the RB in said cancer cells within a range of from 15 to 75 hours in order to span at least one cell cycle, and a minimum effective amount of said enzyme deactivating agents to cause regression of said tumor.

2. A method of treating a patient having a tumor comprising malignant cancer cells having an operative retinoblastoma (RB) protein, by dephosphorylizing the RB protein in said cancer cells and continuously maintaining a dephosphorylated state of the RB in said cancer cells to induce apoptosis thereof, comprising the steps of:

administering to said patient having a tumor comprising malignant cancer cells having an operative retinoblastoma protein a pharmaceutically effective dosage of a drug consisting of disulfram, curcumin, bis-chloronitrosourea (BCNU) and buthionine sulfoximine (BSO) in a pharmaceutically acceptable carrier as needed to cause an increase in intracellular redox potential (E) and decrease in the $[GSH]^2/[GSSG]$ (wherein [GSH] is the concentration of glutathione and [GSSG] is the concentration of glutathione disulfide) ratio in the malignant cancer cells of said tumor and to continuously maintain said decreased $[GSH]^2/[GSSG]$ ratio within a range of from 15 to 75 hours.

* * * * *